United States Patent [19]

Kawamura et al.

[11] Patent Number: 5,346,825
[45] Date of Patent: Sep. 13, 1994

[54] METHOD FOR IMPROVING THE RATE OF CELL FUSION

[75] Inventors: Yoshio Kawamura, Kokubunji; Kazuo Sato, Tokyo; Shinji Tanaka, Akishima; Hiroyuki Kohida, Fuchu; Masatoshi Sakurano, Shimizu, all of Japan

[73] Assignee: Hitachi, Ltd., Tokyo, Japan

[21] Appl. No.: 910,524

[22] Filed: Jul. 8, 1992

Related U.S. Application Data

[63] Continuation of Ser. No. 253,560, Oct. 5, 1988, Pat. No. 5,154,814.

[30] Foreign Application Priority Data

Oct. 7, 1987 [JP] Japan ................................. 62-251494

[51] Int. Cl.$^5$ ................................................. C12N 5/00
[52] U.S. Cl. ................................ 435/240.26; 425/240.1
[58] Field of Search ................ 435/173, 240.26, 172.2, 435/240.1

[56] References Cited

U.S. PATENT DOCUMENTS 4,894,343  1/1990  Tanaka et al. ....................... 435/301
4,895,805  1/1990  Sato et al. ............................ 425/286

FOREIGN PATENT DOCUMENTS 153893 of 1984 Japan.

*Primary Examiner*—Douglas W. Robinson
*Assistant Examiner*—Jeffrey J. Sevigny
*Attorney, Agent, or Firm*—Antonelli, Terry, Stout & Kraus

[57] ABSTRACT

The following invention relates to an apparatus and a method for improving the rate of cell fusion. Cells contained in chambers are prevented from adhering to the surface of the walls of a chamber in which they are contained by the pulse-like changes in fluid pressure, which causes the cells to separate from the surface of the chamber.

5 Claims, 2 Drawing Sheets

METHOD FOR IMPROVING THE RATE OF CELL FUSION

This is a continuation of application Ser. No. 07/253,560, filed Oct. 5, 1988, now U.S. Pat. No. 5,154,814.

BACKGROUND OF THE INVENTION

This invention relates to a cell handling apparatus, and in particular, to a cell fusion apparatus suited for effecting one-to-one fusion of cells.

In a conventional cell fusion apparatus, for example, as described on pages 845 to 846 of the collection of treatises of the academic in the spring meeting of the Japan Society of Precision Engineering in 1987, different types of cells are supplied one by one to chambers arranged in a matrix-like manner, and the cells are fixed to respective small slits of the chambers by absorbing them with absorption nozzles so as to effect cell fusion in each chamber.

In the above-described prior art, no consideration is given to the phenomenon that cell membranes adhere to walls of the chambers when they rest thereon for long periods of time so that the cell fusion rate cannot be improved.

SUMMARY OF THE INVENTION

It is an object of this invention to improve the cell fusion rate of a cell handling apparatus by preventing the cell membrane from adhering to the chamber walls so that damage to the cells may be avoided.

The above object can be attained by applying for a short time a mechanical or a hydrodynamical force to the cells fixed in the chambers by absorption so that the same portion of a cell may not remain in contact with the wall surface over a certain period of time.

In order to overcome the problem in the prior art, a compression device is provided in the absorption system which is arranged below the chambers. This compression device serves to apply fine pressure to the cells periodically. Since this periodically applied pressure exceeds the absorption pressure, the cells which have been fixed to the slits by absorption are separated therefrom. As the fine pressure is applied in the form of pulses, the cells are not driven out of the chambers but fall down on the slits again by absorption. By repeating this operation, the same cell portions can be prevented from remaining in contact with the chamber walls for a long period of time.

DETAILED DESCRIPTION OF THE PREFERRED EMBODIMENTS

Figure 1:
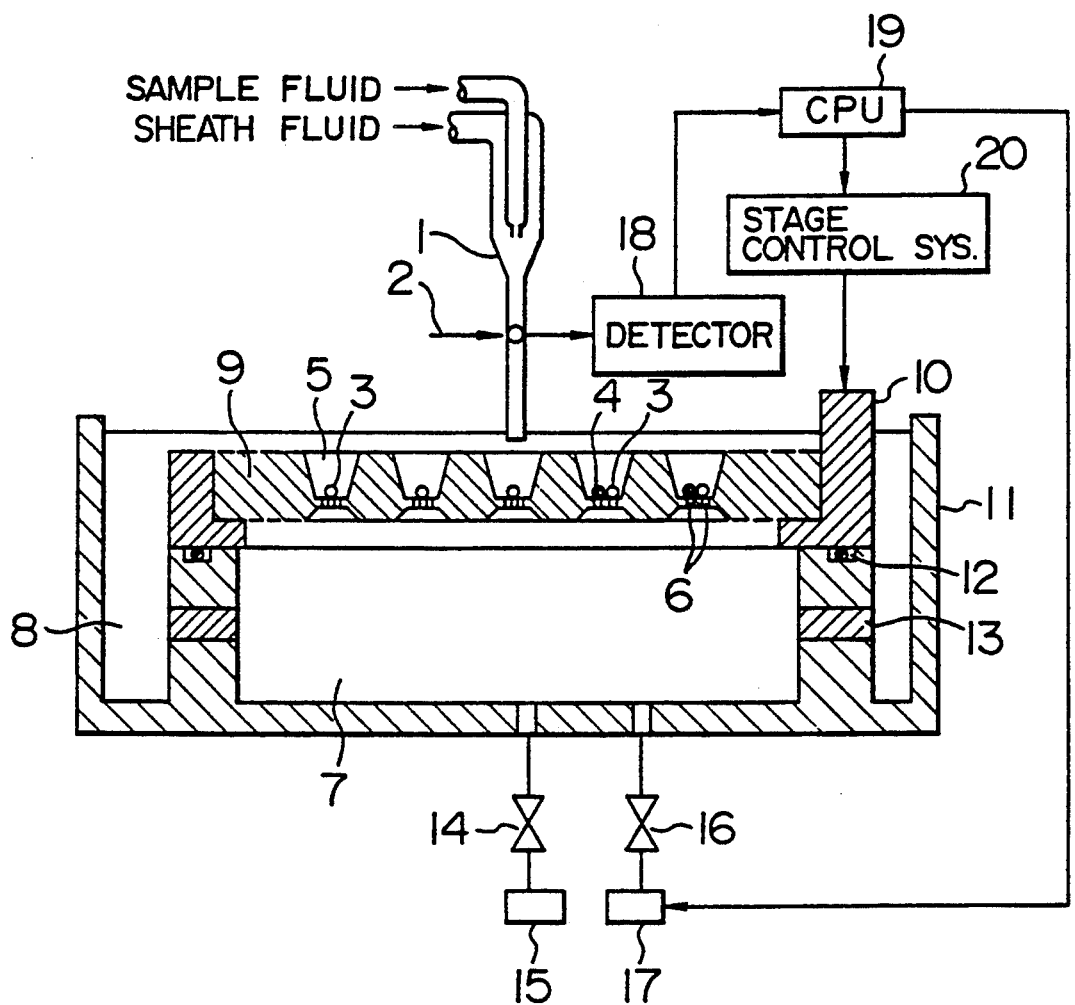
FIG. 1 is a schematic view of the cell fusion apparatus in accordance with an embodiment of this invention.

An embodiment of this invention will now be described with reference to FIG. 1.

As shown in the drawing, the apparatus is composed of a flow cell 1 for pouring cells, chambers 5 for respectively receiving cells, an absorption vessel 7 for fixing and holding the cells, a detector 18 for sorting the cells, a stage (not shown) for moving the chambers to a position under the flow cell, an absorption pump 15 for generating negative pressure in the absorption vessel, 7 and a pressurizing pump 17 for applying pressure in the form of pulses to the absorption vessel 7. A silicon wafer 9 on which fine chambers 5 are arranged in a matrix-like manner is mounted on a holder 10 and arranged in a vessel 11 on an XY-stage (not shown). Each chamber 5 has a square inlet whose sides are 670 $\mu$m long with, a depth of 365 $\mu$m, and a square bottom whose sides are 150 $\mu$m. The vessel 11 is filled with a sorbitol as an isotonic solution having a density suited for the cells 3 and 4. The absoroption vessel 7 is defined by fixing the holder 10 to which the wafer 9 having the chambers 5 is adhered, by an O-ring 12 in the stationary section of the vessel 11. The cells 3 and 4 are poured into the chambers 5 by means of the flow cell 1, one pair for one chambers 5.

First, the first cells 3 alone are put in a cell sample liquid and are poured, together with a sheath liquid, into the chambers 5 arranged in a matrixlike manner, one by one, by means of the flow cell 1. Provided in the passage of the flow cell 1 is a detector 18 which is adapted to sort cells optically. The passage of the flow cell 1 is irradiated with a laser beam 2 from a light source (not shown). The detector 18 receives light beam 2 scattered by the particles flowing in the passage, and judges whether the particles in the passage are the required cells or irrelevant particles such as dust. When the passing of the required cells has been detected, the XY-stage is driven through a CPU 19 and a stage control system 20 so as to position a predetermined chamber 5 directly under the flow cell 1, thereby enabling one of the first cells 3 to be poured into the chamber 5. By repeating this operation, the first cells 3 are poured into all the chambers 5. Subsequently, the second cells 4 alone are put in a cell sample liquid, and a similar operation is performed. As a result, each of the chambers 5 is furnished with a pair of cells 3 and 4.

Figures 2A, 2B, 2C, 2D:
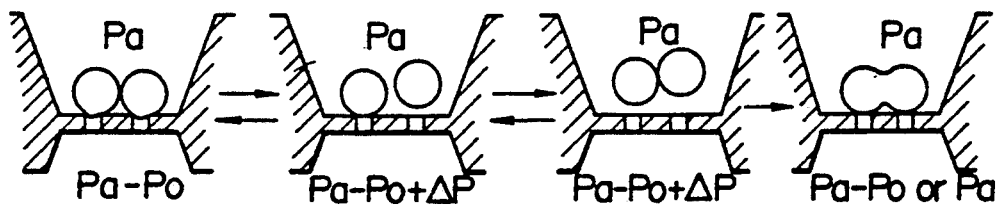
FIGS. 2A, 2B, 2C and 2D illustrate the behavior of a pair of cells in a chamber of the apparatus according to the invention.
Figure 3:
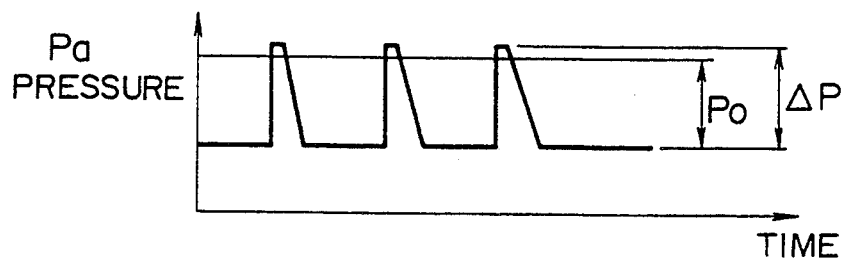
FIG. 3 shows a waveform representing the pressure condition in the absorption vessel of the apparatus according to the invention.

Provided at the bottom of each chamber 5 is a slit 6 having a smaller dimension than the cells 3 and 4. The fluid in the chamber 5 is absorbed through this slit 6. As a result, the cells 3 and 4 in each chamber 5 are absorbed by this slit 6 and fixed thereto, as shown in FIG. 2A. Suppose the pressure in the upper section of the chamber is Pa, the difference in absorption pressure Pa−Po may be appropriately set at 5 to 20 mmHg. The absorption pressure is adjusted to a predetermined value by means of the absorption pump 15 and a pressure regulator 14. Furnishing of each chamber 5 with a pair of cells, which has been described so far, can be effected also with the prior art apparatus. However, it has been made clear that when, after being poured, the cells remain in contact with the slit as shown in FIG. 2A for a long time, the cell membrane may be damaged. In order to overcome this problem, this invention provides a mechanism which is adapted to apply a predetermined pressure to the absorption vessel 7 by means of a pressurizing pump 17 so as to separate the cells from each slit 6 by a microscopic distance. The pressure $\Delta$P of the pressurizing pump 17 is applied to the absorption vessel, as shown in FIG. 3, after being adjusted to a predetermined value through a pressure regulator 16. Suppose the absorption pressure is Po and the pressure in the upper section of each chamber is Pa, the application of pressure is periodically effected in such a manner that the pressure below the chamber slit 6 ($Pa - Po + \Delta P$) becomes a positive pressure. As a result, the pair of cells are upwardly separated from the slit 6, as shown in FIGS. 2B and 2C. When, after the separation of the cells, the applied pressure disappears, the pair of cells fall down on the slit 6 by the absorption pressure to be close to each other. While the separation and the absorption are alternately repeated, a fusion promoting effect is performed on the atmosphere around the cells, so that the pair of cells are fused together, as shown in FIG. 2D. Depending on the cells used, the operation of absorption and pressurization may be stopped to effect cell fusion. In particular, cells which have been fused together are subject to damages for a certain period of time after the fusion. Accordingly, it is preferable that the absorption pressure is reduced to zero immediately after the fusion and a fine positive pressure which enables the cells to float exclusively within the chamber is applied.

As have been described above, in this invention, the operations of fixing the cells to the slits 6 and separating them therefrom as shown in FIGS. 2A, 2B and 2C are repeated, so that damages to the cells, which may otherwise be caused when the same portions thereof remain in contact with the slits 6 for a long period of time, can be avoided.

While in the above embodiment the cells on each slit 6 are separated therefrom by the pressurizing force only, it is also possible to use mechanical fine vibration additionally. In this case, according to the invention, a piezoelectric material 13 is arranged around the absorption vessel 7 so as to promote the separation of the cells from the slits 6 by electrifying the material 13 periodically. To this end, a well-known ultrasonic oscillator may be employed alternatively.

As the fusion promoting effect, such a measure as adding some PEG (polyethylene glycol) which is a fusion promoter, may be taken, or the cell fusion may be promoted by providing electrodes in the vicinity of the chambers so as to apply an appropriate electrostatic field thereto, thereby causing each pair of cells to be fused together by dielectrophoresis. As to the configuration and the material of the chambers 5, it will be understood that other structures than those described above may be employed.

When buoyancy acts on the cells because of the specific weight difference between the cells and the solution around them, this could be easily overcome by turning over the silicon wafer 9 shown in FIG. 2 so that the chambers 5 may be faced downward.

Figure 4:
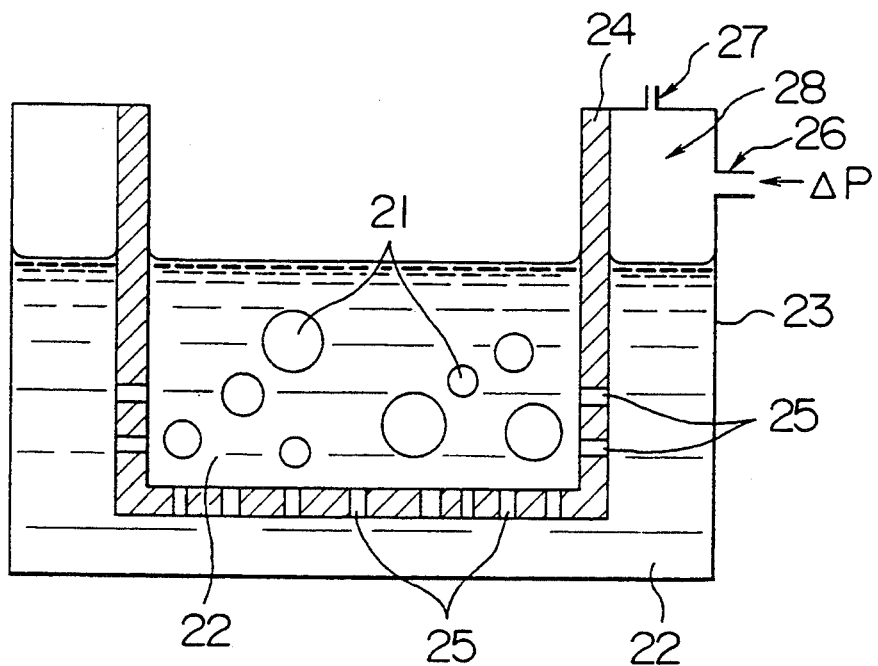
FIG. 4 is a schematic view of the cell handling apparatus in accordance with another embodiment of this invention.

Another embodiment of this invention will now be described with reference to FIG. 4. According to this embodiment, there is provided a vessel which has a wall 24 formed with a multitude of fine through apertures 25 and a space 28 surrounding the wall 24, the inner space defined by the wall 24 receiving cells 21 and a solution 22 suited to activating the cells. The space 28 defined by the wall 24 and an outer wall 23 communicates with the atmospheric pressure exclusively through a leak hole 27. The space 28 is provided with a pressurizing hole 26 for applying a fine pressure. The cells 21 in the vessel sink to the bottom wall because of the difference of specific gravity or are brought into contact with the side wall 24 by the main stream of the solution. When a predetermined pressure is applied through the pressurizing hole 26 in a pulselike manner, the pressure in the space 28 rises rapidly, causing the solution to flow into the inner space of the vessel through the apertures 25, which enables the cells to be kept separating from the wall 24. The pressure in the space 28 which has risen rapidly is gradually reduced by the leakage through the leak hole 27. The back flow of the solution through the apertures 25 due to this leakage can be made very slow by adjusting the opening of the leak hole 27, so that it does not cause the cells to be brought into contact with the wall 24 again. Instead of the solution 22, the space 28 may be filled with a gas, which is injected into the inner space of the vessel as foam. Further, instead of pressurizing the space 28, suction may be applied to the inner space of the vessel in which the cells 21 are disposed so that the pressure therein may become lower than the atmospheric pressure, thereby causing the solution to flow through the apertures 25.

In accordance with this invention, cells which are disposed in pairs in the chambers can be held therein without being in contact with the chamber walls for a long period of time and yet without getting out of the chambers, thereby enabling the cells to be handled without being damaged.

What is claimed is:

1. A method of improving the rate of cell fusion comprising the steps of:
   (a) providing a first vessel having at least one chamber for receiving cells, the at least one chamber having a bottom wall and at least one slit formed therein;
   (b) providing a second vessel in communication with the at least one chamber through the at least one slit, the at least one slit being smaller in size than a size of the cells received therein;
   (c) supplying an isotonic solution into the first vessel;
   (d) supplying cells having a cell membrane into the at least one chamber;
   (e) holding the cells in contact with a bottom wall surface around the at least one slit in the at least one chamber and providing isotonic solution in the second vessel;
   (f) separating from the bottom wall surface the cells which were held in contact with the bottom wall surface around the at least one slit by transferring the isotonic solution from the second vessel through the at least one slit into the at least one chamber; and
   (g) repeating the cell holding step (e) and the cell separating step (f) alternately until cell fusion occurs.

2. The method of claim 1, wherein the cell holding step (e) is carried out by transferring the isotonic solution from the chamber into the second vessel.

3. The method according to claim 1, wherein the cell supplying step (d) includes pouring the cells and a sample fluid into the at least one chamber of the vessel.

4. A method of improving the rate of cell fusion comprising the steps of:
   (a) providing at least one slit in at least one wall of a chamber arranged for receiving cells therein;
   (b) supplying cells to the at least one chamber;
   (c) supplying a fluid to the at least one chamber;
   (d) holding cells within the at least one chamber adjacent to the at least one wall of the chamber by drawing fluid through the at least one slit of the at least one chamber; and
   (e) periodically separating the cells held adjacent to the at least one wall of the chamber away from the at least one wall of the chamber and into the at least one chamber so that membrane surfaces of the cells are not in continuous contact with wall surfaces of the at least one chamber until cell fusion occurs.

5. The method according to claim 4, wherein the step (e) of periodically separating the cells away from the at least one wall of the at least one chamber is carried out by generating a positive pressure which is supplied to the at least one slit with respect to fluid in the at least one chamber so as to cause the fluid to flow into the at least one chamber.

* * * * *